United States Patent [19]

Lucas-Dean et al.

[11] Patent Number: 5,766,177
[45] Date of Patent: Jun. 16, 1998

[54] RONGEUR

[75] Inventors: Rob G. Lucas-Dean, San Leon; Michael M. Withey, Pearland; Kent D. Copeland, Houston, all of Tex.

[73] Assignee: Oceaneering International, Inc., Houston, Tex.

[21] Appl. No.: 843,758

[22] Filed: Apr. 21, 1997

Related U.S. Application Data

[63] Continuation-in-part of Ser. No. 626,509, Apr. 2, 1996, abandoned.

[51] Int. Cl.⁶ .................................................. A61B 17/00
[52] U.S. Cl. ........................... 606/83; 606/170; 606/184
[58] Field of Search ............................ 606/83, 170, 205, 606/184

[56] References Cited

U.S. PATENT DOCUMENTS

| | | | |
|---|---|---|---|
| 1,493,240 | 5/1924 | Bohn | 606/170 |
| 4,444,184 | 4/1984 | Oretorp | 128/305 |
| 4,522,206 | 6/1985 | Whipple et al. | 128/312 |
| 4,722,338 | 2/1988 | Wright et al. | 606/83 |
| 4,777,948 | 10/1988 | Wright | 606/83 |
| 4,986,825 | 1/1991 | Bays et al. | 604/22 |
| 4,990,148 | 2/1991 | Worrick III et al. | 606/170 |
| 4,994,024 | 2/1991 | Falk | 604/22 |
| 5,286,255 | 2/1994 | Weber | 604/22 |
| 5,385,570 | 1/1995 | Chin et al. | 606/170 |
| 5,439,474 | 8/1995 | Li | 606/170 |
| 5,451,227 | 9/1995 | Michaelson | 606/83 |
| 5,569,258 | 10/1996 | Gambaze | 606/170 |
| 5,653,713 | 8/1997 | Michelson | 606/83 |

FOREIGN PATENT DOCUMENTS

| | | | |
|---|---|---|---|
| 614647 | 9/1994 | European Pat. Off. | 606/83 |

OTHER PUBLICATIONS

Surgical Aramentarium, V. Muerer, Bapter Healthcare Corporation, 1988 pp. 177, 178, 179, 180, 181, 182,183, 189, 198.

*Primary Examiner*—Michael Buiz
*Assistant Examiner*—Julian W. Woo
*Attorney, Agent, or Firm*—Kurt S. Myers

[57] ABSTRACT

The present invention is directed to a surgical rongeur having a body, a replaceable hollow cutting member and an actuator for moving the cutting member. The body has a distal end and a proximal end. The body at the distal end has an extended member terminating in an anvil. Between the distal end and the proximal end is a hollow portion, and at the proximal end of the body is a handle which actuates the cutting member. The replaceable hollow cutting member is movable within and guided by said hollow portion of the body but extends beyond the body at the proximal end. The hollow cutting member is actuated to cut any bodily material positioned between the anvil of the body and the cutting member, capturing the cut material in the hollow cutting member.

17 Claims, 7 Drawing Sheets

RONGEUR

RELATED APPLICATION

This application is a continuation-in-part application of U.S. Ser. No. 08/626,509, filed Apr. 2, 1996, now abandoned, entitled "RONGEUR".

FIELD OF THE INVENTION

The present invention is directed to a surgical tool particularly useful in the least invasive surgery. More specifically, the present invention is directed to a rongeur having a replaceable tubular cutting member which cuts and captures bodily material such as tissue and/or bone.

BACKGROUND OF THE INVENTION

Surgical tools may have hollow cutting members, but there are no tools having the simplicity nor the advantageous structure of the rongeur of the present invention.

U.S. Pat. No. 1,493,240 discloses a surgical bone cutter and extractor. The operation of the instrument is by turning barrel 15 and rod 19 in opposite directions.

U.S. Pat. No. 4,444,184 discloses a surgical instrument for operating on joints. A cylindrical manipulator shaft 5 and knife 9 which is integral to the shaft move within a hollow body 1. A slide 10 prevents rotation during the cutting operation.

U.S. Pat. No. 4,522,206 discloses a surgical instrument. The cutting is done by jaws 2, 4 which are operated by actuating member 8.

U.S. Pat. No. 4,722,338 discloses a rongeur having a jaw mechanism comprised of a barrel member having a honed cutting edge on one extremity thereof and having a shaft member located within and arranged for reciprocal motion.

U.S. Pat. No. 4,777,948 discloses a rongeur with a pistol-shaped main frame having a hollow, tubular cutting element releasably clamped at the forward end of the barrel of the frame. A rod slidably received in the barrel projects beyond the front end of the cutting element and has a rearwardly facing shoulder which can be drawn into the cutting element to shear bone or other material engaged between the shoulder and sharpened forward edge of the cutting element. The rod member may be selectively located in any of four rotative orientations for up-cutting, down cutting or side cutting from either side.

U.S. Pat. No. 4,986,825 discloses a surgical cutting instrument. Movable and stationary jaws at the distal end of an elongate probe are actuated by an inner tubular rotatable member.

U.S. Pat. No. 4,990,148 discloses a rongeur with a transverse groove at the intersection of the anvil surface of the base plate and the shank base plate. Also the base of the footplate recess is offset from the shank base plate and the inside wall of the recess meets the recess base in a gentle curve.

U.S. Pat. No. 4,994,024 discloses arthroscopy hook-clippers. A circular cross-section outer shaft is formed with a fixed clipper jaw 4. Within this shaft is a thrust rod with a movable clipper jaw 11 and a vacuum extraction channel.

U.S. Pat. No. 5,286,255 discloses surgical forceps. The forceps include an elongate probe formed of an outer tubular member and an inner member movable in the outer probe member, stationary and movable jaws coupled with the distal ends, respectively, of the outer and inner probe members, and a handle squeezable to move the movable jaw relative to the stationary jaw.

U.S. Pat. No. 5,385,570 discloses a surgical cutting instrument. The instrument comprises outer and inner cutting members 12, 14, respectively. The inner member 14 is fixed at its proximal end to housing 28. Outer cutting member 12 is moved in a longitudinal direction by means of hand manipulation of elongated lever 30.

U.S. Pat. No. 5,439,474 discloses a morcellator system. The device comprises a cutting assembly 10 and a handle assembly 15. The cutting assembly has an outer tube 100 and an inner tube 200. The cutting tubes 100 and 200 are constructed in the handle assembly 15 such that spring 485 normally biases inner tube 200 forward relative to outer tube 100 so that inner tube bottoms out in annular groove 130 and the opening 120 is closed off by inner tube 200. Squeezing members 405 together will cause inner tube 200 to retreat relative to outer tube 11 so that opening 120 will be opened up.

U.S. Pat. No. 5,451,227 discloses a thin foot plate multi bite rongeur. The device consists of a body 10 which has a rear handle 12 and a long shaft 14 terminating at its distal end in a foot plate 16. A hollow slide assembly 20 with T-shaped runner 24 is slidably mounted in slot 24 formed in shaft 14. A safety mechanism 100 is between the slide assembly 20 and the actuating handle of the device.

U.S. Pat. No. 5,569,258 discloses a rongeur with top and bottom parallel bars in sliding relation, one to the other, with the ends cooperating to form cutting tips.

European Patent Application No. 94301639.4 discloses a cannula which comprises a tubular body member having an interior instrument passage and a tissue manipulating surface at the end which will be inserted into the patient's body. The tissue manipulating surface extends radially outwardly from the tubular body member.

None of the rongeurs illustrated in the Baxter catalogue have a cutting member which is tubular and disposable. The rongeurs of the present invention permit more than one cut to be made with the same instrument without removal from the patient and collects the cuttings in the cutting member for examination or other use or for easy disposal.

SUMMARY OF THE INVENTION

The present invention is directed to a surgical rongeur having a body, a tubular cutting member and actuating means for moving the cutting member. The body has a distal end and a proximal end. The body at the distal end has an extended member terminating in an anvil and between the distal and proximal ends is a tubular portion and at the proximal end are handles that actuate the cutting member. The tubular cutting member is movable within and guided by the tubular portion of the body and extends beyond the body at the proximal end. The tubular cutting member is actuated to cut any bodily material positioned between the anvil of the body and the cutting member, capturing the cut material in the tubular cutting member.

BRIEF DESCRIPTION OF THE DRAWINGS

FIG. 7 is an isometric partial view of the body of the rongeur of FIG. 6; specifically illustrating the threaded connection which permits the distal end of the body to be rotated.

DESCRIPTION OF THE PREFERRED EMBODIMENTS

Figure 1:
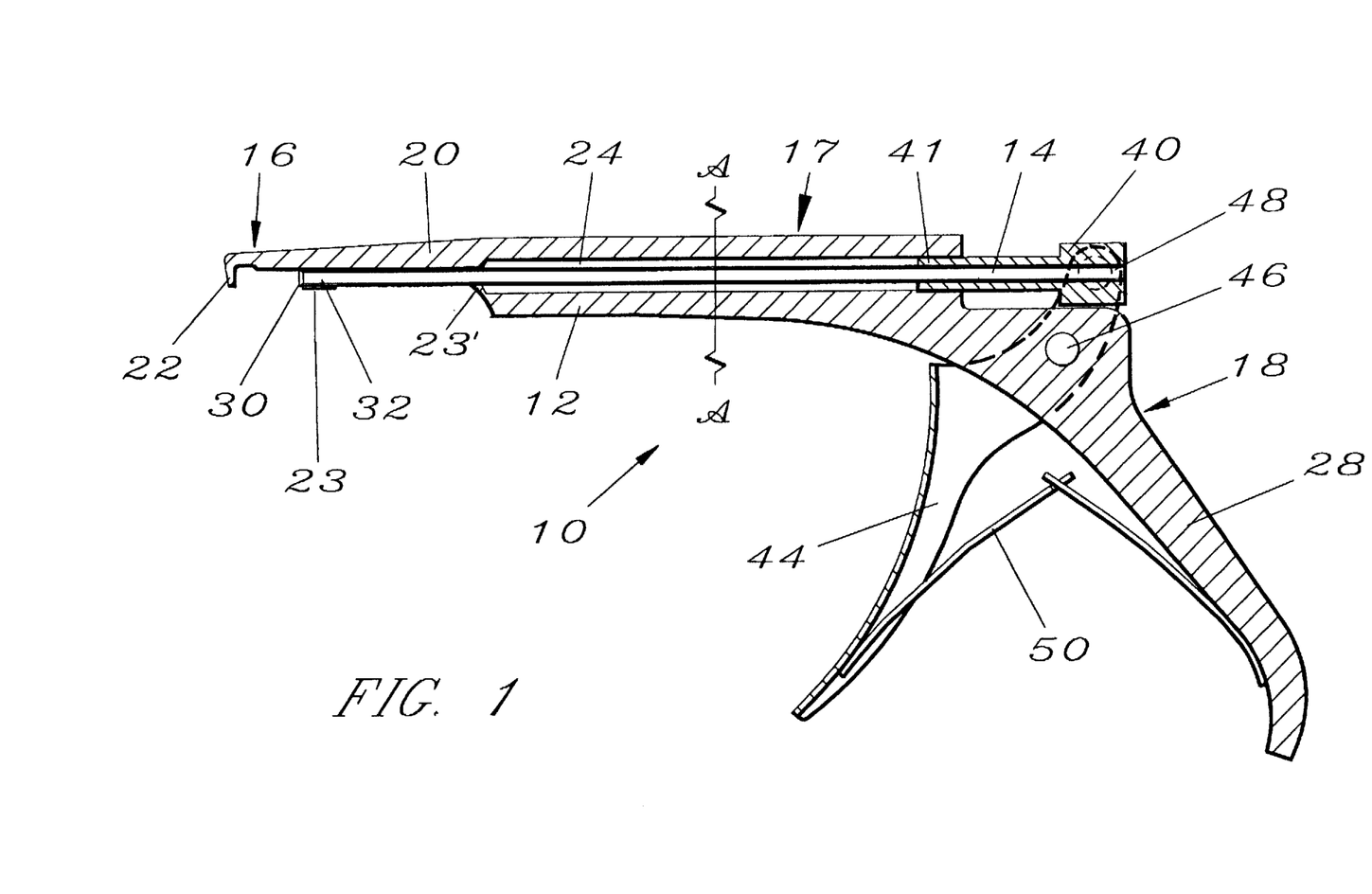
FIG. 1 is a cross-sectional view of one embodiment of the rongeur of the present invention.

Referring now to FIG. 1, one embodiment of a rongeur 10 of the present invention comprises a body 12 and a cutting member 14. The body 12 has a distal end 16 and a proximal end 18. Between the distal end 16 and the proximal end 18 is a tubular portion 17 of the body 12. At the distal end 16 of the body 12 is an elongated or extended member 20 that terminates in an anvil 22. As shown in FIG. 1, anvil 22 is at a right angle (90° downward) to the elongated member 20. The size of anvil 22 is at least as great as the size of the distal end of cutting member 14. Elongated member 20 extends from the tubular or hollow portion 17 of the body 12 which has an opening 24 for the cutting member 14 to pass through and structurally supports the cutting member 14. The distal and proximal ends of cutting member 14 terminate outside the body 12, passing through the tubular portion 17. The tubular portion 17 of the body 12 has a support member 23 positioned a distance from the anvil 22 such that any bending moment caused during the cutting will not permit the cutting member 14 to bend the support member 23 may be a ring or other structure to support the cutting member 14 at a point less than two inches from the anvil 22. Alternately, the tubular portion 17 of the body 12 may have more than one diameter along the length of the longitudinal axis of the opening 24 so as to form a support member 23'. The proximal end 18 of the body 12 terminates in a handle 28, as shown in this embodiment at an angle downward from the longitudinal axis of the opening 24.

The cutting member 14 is a hollow preferably cylindrical tube. The preferred material of construction is a steel which can be sharpened. The cutting member 14 is movable within the hollow portion 17 of the body 12 and is easily replaceable. The distal end 30 is preferably beveled to a sharp cutting edge. When bodily material, such as bone, is placed between the distal or cutting end 30 of the cutting member 14 and the anvil 22, the cutting member 14 will cut and capture the bodily material in the passageway or opening 32 of the cutting member 14. The advantage of the passageway 32 or a hollow, tubular cutting member 14 is first, that the bodily material is cut rather than sheared or torn and second, that more than one cut may be made without withdrawing the rongeur from the patient. Further, the cut material is captured in the passageway 32 and may be used for testing or used in another procedure such as bone grafting.

Another advantage of the tubular cutting member 14, which is easily insertable into the hollow or tubular portion 17 of the body 12, is that it may be replaceable and/or disposable. The cutting member 14 may be made of surgical stainless steel or a much cheaper material such as ordinary carbon steel or engineering plastic. The remainder of the rongeur 10 of the present invention, other than the cutting member 14, may be made from any appropriate commercial material including steel or plastic. Because of its simple construction, if cheaper materials of construction are used, it may permit the remainder of the rongeur to also be disposable. Alternatively, the remainder of the rongeur may be made of materials that can be sterilized and reused.

The activation or movement of the cutting member 14 is preferably based on a simple lever principle. A lever connector 40 for moving the cutting member or tube 14 in the body 10 of the rongeur is located at the proximal end of the tubular cutting member 14. The connector 40 in the embodiment of FIG. 1 is a drive sleeve or shaft 41 having bearing pins 42 on the outside of an enlarged potion of the drive sleeve 41. The cutting member 14 may be force fit into the drive sleeve 41 of connector 40. Alternatively, a single bearing pin 42 which passes through the drive sleeve 41 of connector 40 and which also passes through the cutting member 14 may be used. However it is preferred that two pins 42 are used so that the opening 32 in the cutting member 14 remains open for inserting a cleaning rod, which will be discussed in more detail hereinafter. Both the drive sleeve 41 of connector 40 and the cutting member 14 move integrally together and the cutting member 14 is actuated when force is applied to the bearing pin or pins 42. A second handle 44 is attached to the body 12 by a pivot pin 46. The upper portion of the handle 44 has a bearing surface 48 that bears against bearing pins 42. As the handle 44 is squeezed toward the handle 28 of the body 12, the force is transmitted through the bearing pins 42 and bearing surface 48 or bearings to move the cutting member 14 toward the anvil. Upon release of the pressure between the two handles, a spring, such as leaf spring 50, moves the cutting member 14 away from the anvil.

Figure 1A:
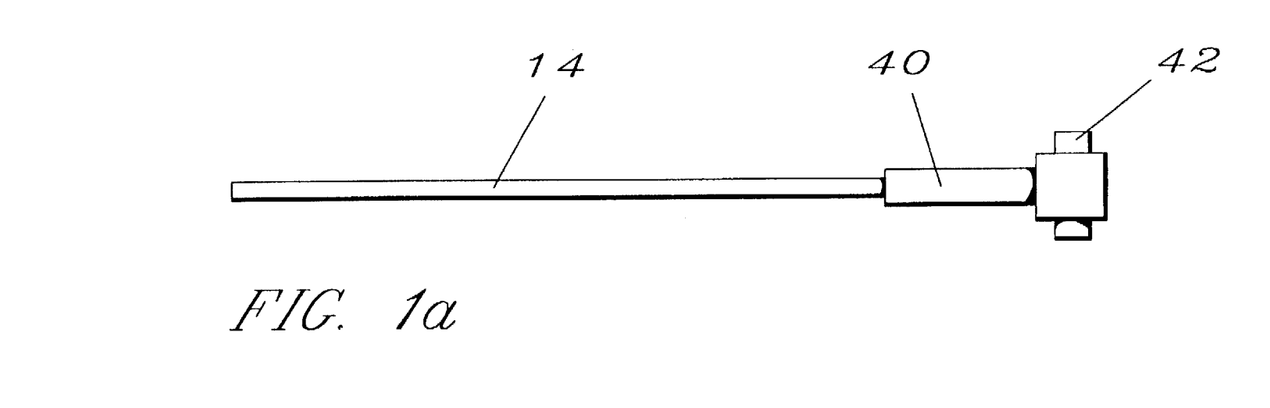
FIG. 1A is a top view of an embodiment of the replaceable tubular cutting member connected at its proximal end to a drive member.

In FIG. 1A the cutting member 14 is shown as force fit into the connector or drive member 40 and the cutting member 14 and the connector 40 are a single unit. In this embodiment, the unit can be replaced or disposed as a unit. A disposable cutting member 14 or unit has the advantage that no other person is in contact with the material cut from a patient nor the cutting surfaces of the rongeur. Further, the cutting member 14 is easily replaceable in the rongeur.

Figure 1B:
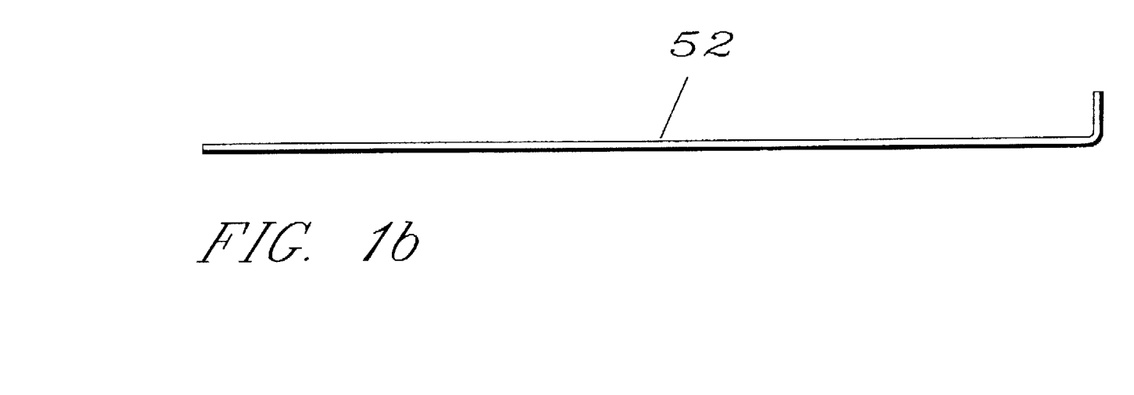
FIG. 1B is a side view of an embodiment of a cleaning element for removing bone and/or tissue from the cutting member.

Referring now to FIG. 1B, a cleaning rod 52 is shown which may be used to remove the material collected in the passageway 32 of the cutting member 14 when the rongeur of the present invention is removed from the patient. The rod 52 may also be used as a measuring device by inserting the rod 52 into the passageway 32 before cutting and the movement of the rod 52 when the cutting is done giving an indication of the amount of material cut from the patient.

Figure 2A:
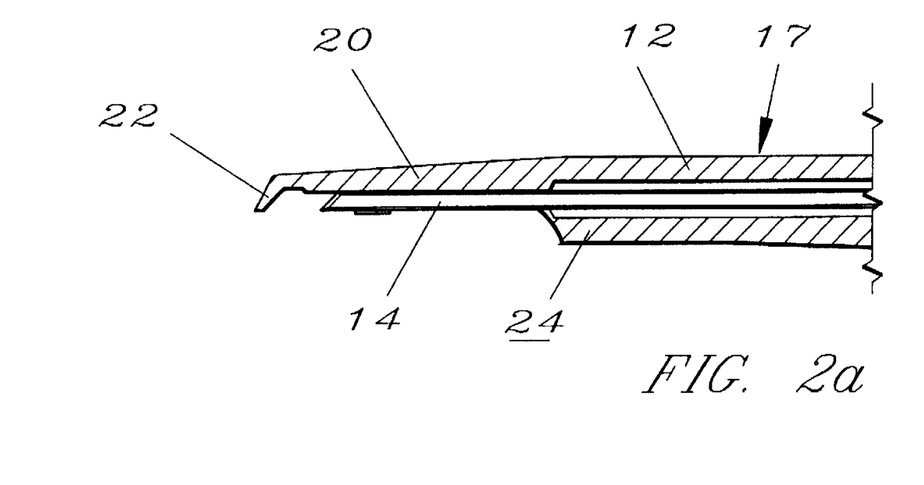
FIGS. 2A and 2B are partial cross-sectional views of the distal end of the rongeur body illustrating other embodiments of the rongeur of the present invention; specifically, the detail of the angle of the anvil.
Figure 2B:
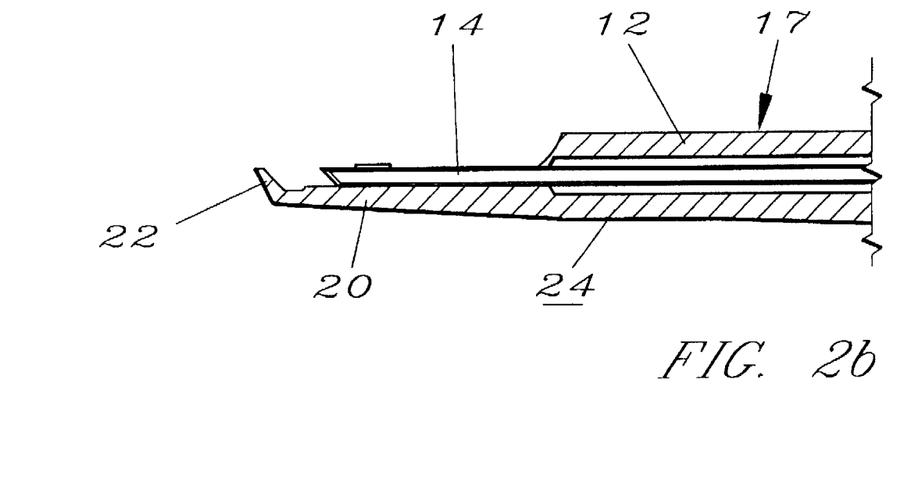

FIGS. 2A and 2B show other embodiments of the rongeur of the present invention. Common to both embodiments is that the anvils 22 are at an angle different than shown in FIG. 1. In FIG. 2A, the elongated member 20 extends from the top of the tubular portion 17 of body 12 and the anvil extends downwardly from the elongated member 20. In contrast, in the embodiment of FIG. 2B, the elongated member 20 extends from the bottom of the tubular portion 17 of body 12 and the anvil 22 extends upwardly from the elongated member 20. These two figures of drawings illustrate that different configurations of the rongeur of the present invention are desirable or required depending on the location of the material being cut in the patient. The specific design of the rongeur chosen takes into account whether the material to be cut in the patient will be from the top, the bottom or either side.

Figure 3:
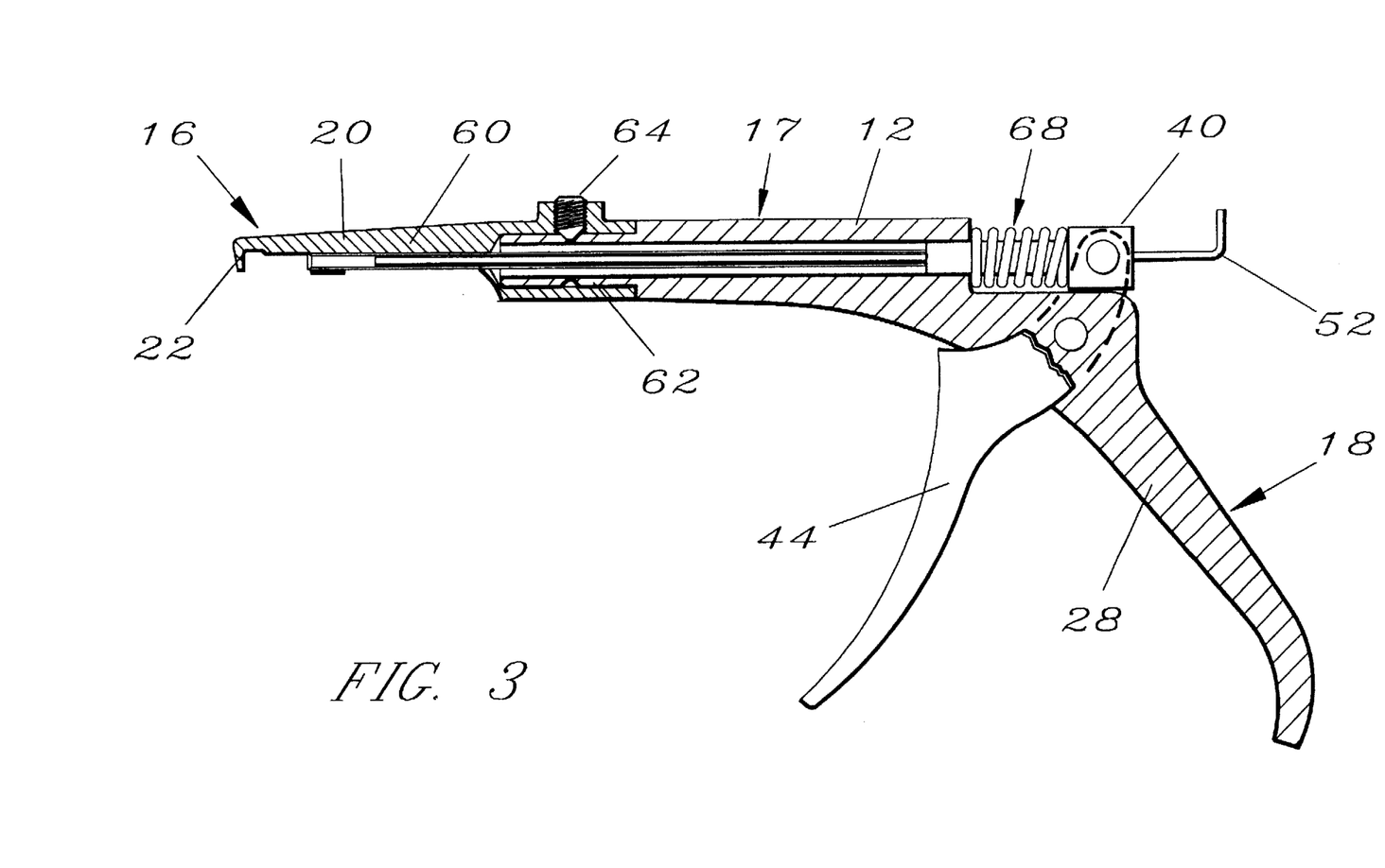
FIG. 3 is a partial cross-sectional view of another embodiment of a rongeur of the present invention.

Referring to FIG. 3, another embodiment of the rongeur of the present invention is shown which allows the elongated member 20 to be rotated to any desired position with respect to the handles. This embodiment of the rongeur eliminates the necessity of having two or more embodiments with a fixed single piece body such as illustrated in FIGS. 2A and 2B. The rongeur body 12 of this embodiment is constructed in two pieces. One piece is the tubular portion 17 of the body 12 and the proximal end 18 with the handle 28. The other piece is a rotating distal end 16 with a rotatable member 60 including elongated member 20. The rotating member 60 in this embodiment is shown fixed to a reduced nose 62 of the tubular body 17 by set screw 64. The advantage of this embodiment is that the surgeon with a small allen wrench or screwdriver or other tool may set the position of the anvil 22 in any desired relation to the handles 28 and 44.

Another feature of the rongeur illustrated in FIG. 3 is the use of a common coil spring 68 positioned between the enlarged head on connector 40 and the tubular body 17 of the body 12. The spring 58 retracts the cutting member 14 from the anvil 22 when the squeezing of the handles is released.

Figures 4A, 4B, 4C, 4D:
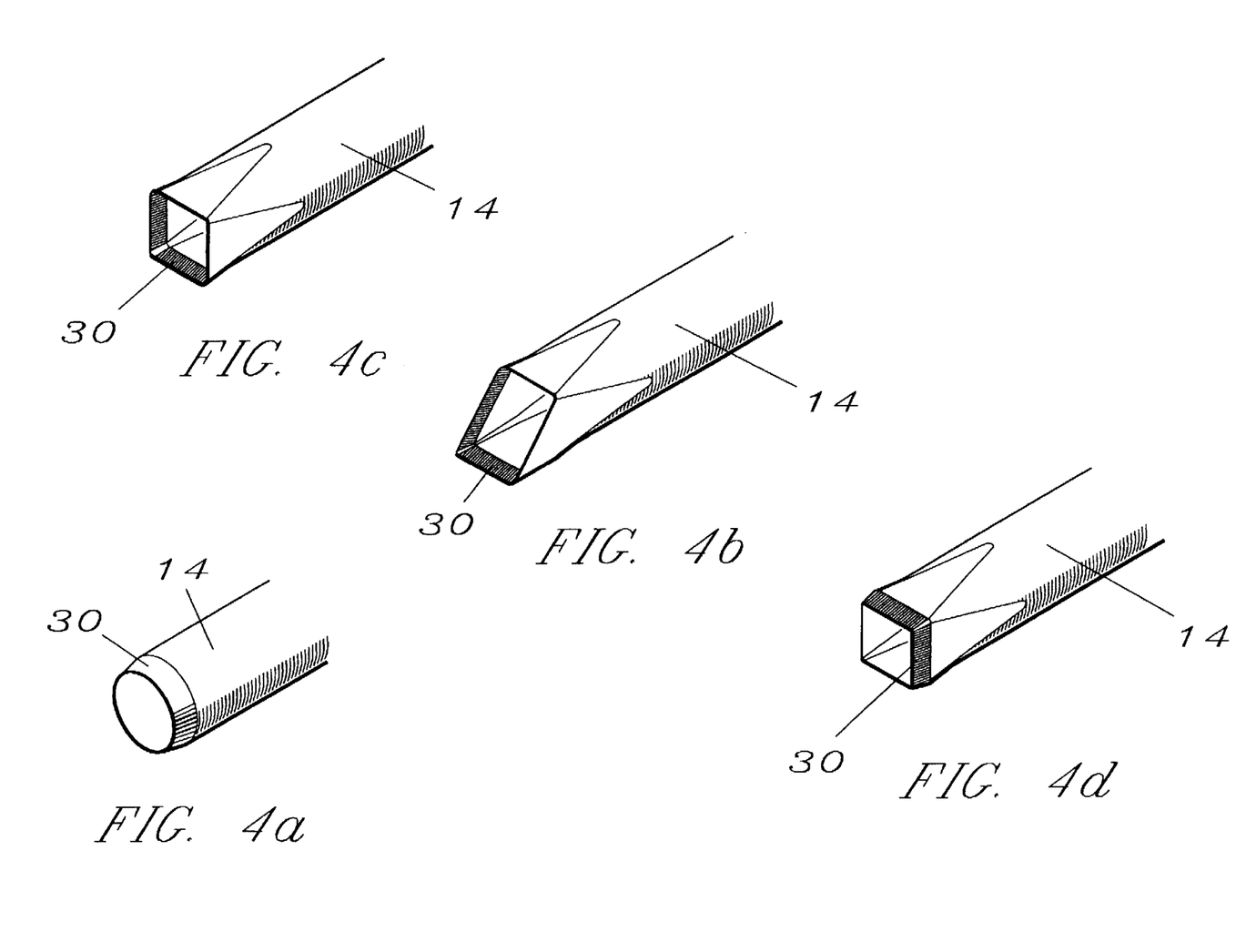
FIGS. 4A, 4B, 4C and 4D are partial isometric views of different embodiments of the cutting member of a rongeur of the present invention; specifically, the detail of the shape of the tubular member and sharpening or beveling either the inside surface or the outside surface.

Referring to FIGS. 4A, 4B, 4C and 4D, these figures illustrate that the geometry of the distal or cutting end 30 of cutting member 14 may be other than cylindrical, as shown in FIG. 4A. FIG. 4B illustrates that the distal end 30 of the cutting member 14 may be cut at an angle to the axis of the cutting member 14. This feature may be of importance when the anvil 22 of the rongeur is at an angle such as shown in FIGS. 2A or 2B. This embodiment also illustrates that the distal end 30 may be sharpened to a non-circular or elliptical cross-section as compared to the circular cross-section shown in the embodiment of FIG. 4A. The embodiments of FIGS. 4C and 4D illustrate that the distal end 30 of the cutting member 14 may be beveled either on the inside or the outside of member 14, respectively.

Figure 5:
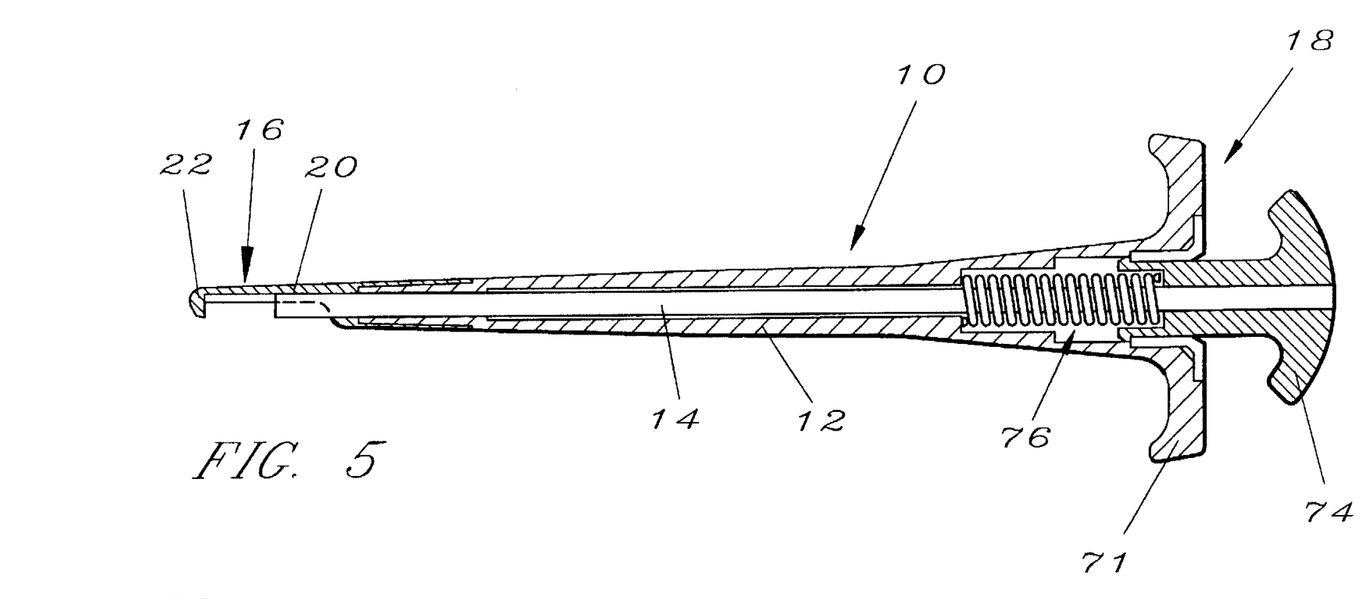
FIG. 5 is a partial cross-section of still another embodiment of a rongeur of the present invention.
Figure 5A:
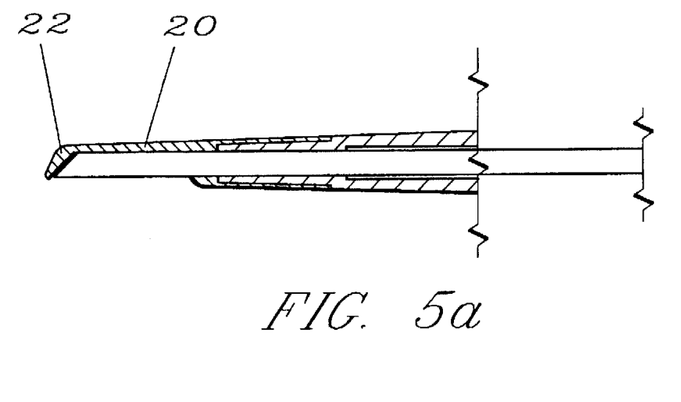
FIG. 5A is a partial cross-section illustrating another angle of the cutting member and the anvil.

FIG. 5 discloses still another embodiment of the rongeur of the present invention. In this embodiment, rongeur 10 comprises a body 12 and a cutting member 14. At the distal end 16 of the body 12 is an elongated member 20 which terminates in an anvil 22. However, the body 12 at the proximal end 18 terminates in a handle or finger grasper 71. The second handle is a hand piece 74 that is on the end of the cutting member 14. The cutting member 14 is moved toward the anvil 22 when the hand piece 74 is forced toward the body 12 cutting any bodily material between the anvil 22 and the end 30 of the cutting member 14. A spring 76 between the body 12 and the hand piece 74, which acts as the drive member, retracts the cutting member 14 when the squeezing pressure between the finger grasper 71 and the hand piece 74 is released. FIG. 5A illustrates that the angle of the anvil may be any desired angle.

Figures 6, 6A:
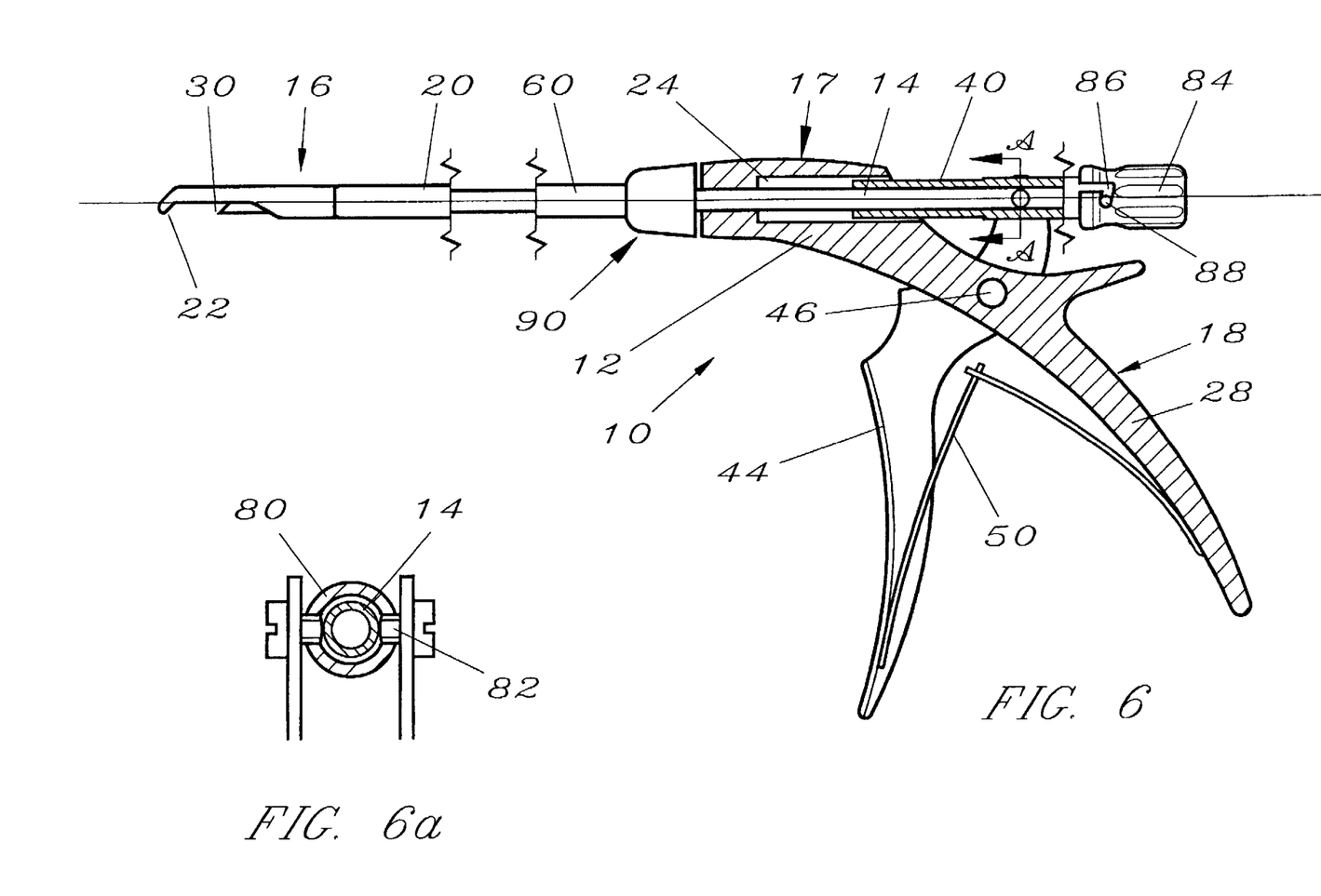
FIG. 6 is a cross-sectional view of still another embodiment of a rongeur of the present invention.

Referring now to FIG. 6, this embodiment of the rongeur illustrates that a different connector 40 or rotatable member 60 than shown in FIG. 1 may be used. The connector 40 in this embodiment comprises a drive sleeve or shaft 80 that is attached to handle 44 by set screws 82. The set screws 82 also provide a bearing surface for the bearing surfaces of the handle 44. The length of set screws 82 may be such that, as shown in FIG. 6A, they hold cutting member 14 in the drive sleeve 80 so as to move integrally together when the handles 28 and 44 are squeezed, actuating the cutting member 14 toward the anvil 22. Alternately, the cutting member 14 terminates in a quick latch member 84 that slips over drive sleeve or shaft 80 and has at least one J-slot 86. In this embodiment or alternative, the drive shaft 80 has a pin(s) 88 that engages J-slot 86 in the quick latch 84 when the cutting member 14 is slipped into drive sleeve 80 and the latch member 84 is slipped over the drive sleeve 80. When the latch member 84 is rotated the two members are locked integrally together and move integrally together toward the anvil in the operation of the rongeur.

Also shown in the embodiment of FIG. 6 is a different rotatable member 60. This member 60 which is the distal end 16 of the rongeur has an indexed threaded connection 90. Referring to FIG. 7, the distal end 16 has a female threaded member 92 which is threaded to a male member 94 which is part of the tubular portion 17 of the body 12.

We claim:

1. A rongeur which comprises:
    a body having a distal end, a tubular portion and a proximal end, said body at the distal end including an elongated member terminating in an anvil and at the proximal end terminating in handle means;
    a tubular cutting member, said cutting member movable within and guided by said tubular portion and extending beyond said body at said proximal end; and
    means for actuating said cutting member to cut bodily material placed between said anvil and the distal end of said cutting member.

2. A rongeur according to claim 1 wherein said body is a single piece.

3. A rongeur according to claim 1 wherein said body is two pieces, one piece being a rotatable member which includes said elongated member terminating in said anvil and the second piece including said tubular portion and said handle, and
    means to affix said rotatable member to said tubular portion of said second piece.

4. A rongeur according to claim 1 wherein said cutting member is disposable.

5. A rongeur according to claim 1 wherein said anvil extends upward from said elongated member.

6. A rongeur according to claim 1 wherein said anvil extends downward from said elongated member.

7. A rongeur according to claim 1 wherein said cutting member is circular in cross-section.

8. A rongeur which comprises:
    a body having a distal end, a tubular portion and a proximal end, said body at the distal including an elongated member terminating in an anvil and at the proximal end terminating in handle means;
    a tubular cutting member, said cutting member movable within and guided by said tubular portion of said body and extending beyond said body at said proximal end; and
    lever actuating means for moving said cutting member toward said anvil to cut bodily material placed between said anvil and said cutting member.

9. A rongeur according to claim 8 wherein said cutting member is circular in cross-section.

10. A rongeur according to claim 8 wherein said distal end of said body is rotatable.

11. A rongeur according to claim 8 wherein said anvil is at a angle to said elongated member.

12. A rongeur according to claim 8 wherein said lever actuating means comprises:
    a drive sleeve connected to said cutting member and having a bearing surface, and
    second handle means connected to said body by a pivot pin, said handle means having a bearing surface which bears against said bearing surface of said drive sleeve when said handles are squeezed.

13. A rongeur according to claim 12 wherein said cutting member is connected to said drive sleeve.

14. A rongeur according to claim 12 wherein said cutting member has a latch means at the proximal end to connect to said drive sleeve.

15. A rongeur according to claim 14 wherein said latch means has a J-slot and said drive sleeve has a pin for the two members to move integrally together.

16. A rongeur which comprises:

a body having a distal end, a connecting means for connecting to a cutting member, and a proximal end; and a replaceable cutting member consisting essentially of a disposable, hollow tube which is open at both its distal end and proximal end, said distal end being beveled to a sharp edge;

wherein said connecting means consists essentially of a sleeve in which said proximal end of said tube slips into.

17. A rongeur according to claim 16 wherein said replaceable cutting member includes a quick connector on the proximal end of said tube.

* * * * *